US008926526B2

(12) United States Patent
Shuck

(10) Patent No.: US 8,926,526 B2

(45) **Date of Patent: *Jan. 6, 2015**

(54) PATIENT IN VIVO GUT DIAGNOSTIC AND TREATMENT TOOL

(71) Applicant: L. Zane Shuck, Morgantown, WV (US)

(72) Inventor: L. Zane Shuck, Morgantown, WV (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/931,152

(22) Filed: Jun. 28, 2013

(65) Prior Publication Data

US 2014/0162305 A1 Jun. 12, 2014

Related U.S. Application Data

(63) Continuation-in-part of application No. 13/691,169, filed on Nov. 30, 2012, now Pat. No. 8,491,495.

(51) Int. Cl.

*A61B 10/02* (2006.01)
*G01N 33/50* (2006.01)
*A61B 10/00* (2006.01)

(52) U.S. Cl.

CPC ........ *G01N 33/5091* (2013.01); *A61B 10/0038* (2013.01); *A61B 2010/0061* (2013.01)
USPC .......... 600/562

(58) Field of Classification Search

CPC .......... A61B 5/07; A61B 1/041
USPC .......... 600/562; 604/890.1, 891.1
See application file for complete search history.

(56) References Cited

U.S. PATENT DOCUMENTS

| | | | | |
|---|---|---|---|---|
| 2,881,756 | A * | 4/1959 | Crosby et al. | 600/565 |
| 3,057,344 | A * | 10/1962 | Abella et al. | 600/582 |
| 3,118,439 | A * | 1/1964 | Perrenoud | 600/582 |
| 3,485,235 | A * | 12/1969 | Felson | 600/582 |
| 3,528,429 | A * | 9/1970 | Beal et al. | 600/367 |
| 3,683,890 | A * | 8/1972 | Beal | 600/371 |
| 3,688,763 | A * | 9/1972 | Cromarty et al. | 600/572 |
| 4,036,214 | A * | 7/1977 | Bucalo | 600/582 |
| 5,170,801 | A * | 12/1992 | Casper et al. | 600/582 |
| 5,971,942 | A * | 10/1999 | Gu et al. | 600/582 |
| 7,449,001 | B2 * | 11/2008 | Stoltz | 600/582 |
| 7,452,338 | B2 * | 11/2008 | Taniguchi | 600/593 |
| 7,611,480 | B2 * | 11/2009 | Levy | 604/27 |
| 7,686,770 | B2 * | 3/2010 | Cohen | 600/568 |
| 7,717,862 | B2 * | 5/2010 | Stoltz | 600/582 |
| 7,740,595 | B2 * | 6/2010 | Brown | 600/565 |
| 7,938,775 | B2 * | 5/2011 | Rabinovitz et al. | 600/309 |
| 8,195,276 | B2 * | 6/2012 | Uchiyama et al. | 600/424 |
| 8,257,257 | B2 * | 9/2012 | Takizawa et al. | 600/302 |
| 8,343,069 | B2 * | 1/2013 | Uchiyama et al. | 600/562 |
| 8,394,034 | B2 * | 3/2013 | Iddan et al. | 600/582 |
| 8,406,490 | B2 * | 3/2013 | Gat et al. | 382/128 |
| 8,491,495 | B1 | 7/2013 | Shuck | |
| 2001/0051766 | A1 * | 12/2001 | Gazdzinski | 600/309 |
| 2002/0042562 | A1 * | 4/2002 | Meron et al. | 600/361 |
| 2002/0103417 | A1 * | 8/2002 | Gazdzinski | 600/109 |
| 2002/0132226 | A1 * | 9/2002 | Nair et al. | 435/4 |
| 2003/0020810 | A1 * | 1/2003 | Takizawa et al. | 348/68 |
| 2003/0085994 | A1 * | 5/2003 | Fujita et al. | 348/77 |
| 2003/0181788 | A1 * | 9/2003 | Yokoi et al. | 600/160 |
| 2003/0213495 | A1 * | 11/2003 | Fujita et al. | 128/899 |
| 2004/0092825 | A1 * | 5/2004 | Madar et al. | 600/473 |
| 2004/0115877 | A1 * | 6/2004 | Iddan | 438/200 |
| 2004/0122315 | A1 * | 6/2004 | Krill | 600/437 |
| 2004/0204630 | A1 * | 10/2004 | Gilad | 600/160 |
| 2005/0177069 | A1 * | 8/2005 | Takizawa et al. | 600/573 |
| 2007/0173738 | A1 * | 7/2007 | Stoltz | 600/582 |
| 2008/0208077 | A1 * | 8/2008 | Iddan et al. | 600/582 |
| 2009/0143697 | A1 * | 6/2009 | Tanaka | 600/565 |
| 2009/0253999 | A1 * | 10/2009 | Aoki et al. | 600/565 |
| 2010/0249503 | A1 | 9/2010 | Yazawa et al. | |
| 2012/0153981 | A1 | 6/2012 | Arneson et al. | |

FOREIGN PATENT DOCUMENTS

| | | | | |
|---|---|---|---|---|
| JP | 05168639 A * | 7/1993 | | A61B 10/00 |

OTHER PUBLICATIONS

U.S. Appl. No. 13/930,558, filed Jun. 28, 2013, Shuck.

* cited by examiner

*Primary Examiner* — Sean Dougherty
*Assistant Examiner* — Michael C Stout

(57) ABSTRACT

An orally ingestible capsule device with monitoring and control instruments is provided for practicing physicians to use in patient examining rooms. The Capsule is part of an in vivo gastrointestinal tract (GI Tract or Gut) healthcare system with capabilities of delivering medications to any point in the gut, administering them at any time, or autonomously based upon onboard measurements, and simultaneously measuring results, along with extra body function measurements. It is capable of delivering gut medications or autoimmune perturbation substances and simultaneously measure responses and sample gut substances/microbes at application points. Objectives, as part of patient diagnosis, include determining microbe roles in the patient's digestion process, along with toxic substances in contributing to illnesses or diseases, such as gluten sensitivities. Capsule embodiments include a belt with pockets for substance delivery or sampling, lab-on-a-chip devices, chip-based logic, sensor/transducer, control circuits, nanotech devices and data reduction and storage, for efficient, cost-effective diagnostics and treatment in minimal time.

16 Claims, No Drawings

PATIENT IN VIVO GUT DIAGNOSTIC AND TREATMENT TOOL

This application is a continuation in part of U.S. application Ser. No. 13/691,169 filed on Nov. 30, 2012, now U.S. Pat. No. 8,491,495, which claims benefit of U.S. provisional application No. 61/7,272,177 filed on Nov. 16, 2012, the contents of which are incorporated by reference herein in their entirety.

FIELD OF THE INVENTION

The subject invention is a biomedical, bioengineering device and method for clinical use in discovering, analyzing, and bracketing specific biological, microbial colonization, and biochemical endogenous processes in the human gut in a sufficient manner to provide physicians with the diagnostic information needed to prescribe appropriate medications under a variety of gut conditions. Capabilities of the tool also include in vivo administration of said medications, monitoring, and sampling the results for in vitro analysis.

BACKGROUND OF INVENTION

In brief perspective, after 2,000 years using the most advanced technology available anywhere in the world, the actual processes and causes of Celiac, gluten sensitivities, and many other life threatening and taking diseases with origins in the gut, such as those resulting from gluten or other protein effects, remain unknown today. Likewise, there no known medications or procedures that can cure said diseases, and hundreds, if not thousands, of medications are applied to treat only their symptoms. The fecal-oral cycle of pathogens entering the digestive tract has also greatly increased in the U.S. Now, microbial diseases of the gut rank second in humans only to the respiratory system. While in vivo sampling of the respiratory and cardiovascular fluids is routinely performed with minimal cost, patient inconvenience, and time consumption, sampling of the gastrointestinal tract is extremely technology limited. It is estimated that of the more than 10,000 strains of bacteria in the GI tract, and perhaps exceeding more than a trillion in total number, less than 5% have even been identified, much less characterized. This is understandable since critical regions of the gut are inaccessible for in vivo sampling, observation, monitoring, or direct treatment. As in virtually all current in vivo sampling of masses of the human body, analyses are performed in vitro. However, procedures for testing of gut matter, especially below the stomach and lower colon, are routinely in vitro collected samples of feces expelled from the anus after experiencing all of the conditions and biological processes throughout the small and large intestines, and then are in vitro analyzed. At this point any trace of the causative processes from within the areas of origin, such as the small intestine jejunum, are totally camouflaged, modified, or destroyed. In addition, collection of expelled feces itself exposes the samples to aerobic conditions and other potential contamination. Since at this stage the collected stool may be 50% or more microbes of many thousands of species, strains, and other taxonomic levels, tests are not only difficult, but unrevealing and inconclusive. Microbe isolations and species association with any gut phenomena must be performed by in vivo sampling at points of interest in the natural gut environment, and preserving those samples at least for in vivo analysis, and at best, identified and characterized to the extent possible in vivo in the natural or perturbed environment.

Although the principal interest here is human health, the importance of GI tract processes and microbes in all animals needs more emphasis and greater analysis and diagnostic technologies as part of human health considerations. As the world population of all animals increases and food supplies and all aspects of our world population becomes more dense and integrated as a single community, the oral-feces cycles become more important. Waste products from all animals are becoming of greater importance, and microbes of the gut as herein addressed desperately need more attention, and more technology to aid in understanding their roles. Food digestion processes need to be investigated by multidisciplinary physicians and medical personnel and scientists and engineers of many other disciplines to really analyze the many gut processes in totality, including the roles of some 10,000 species of microbes, along with other patient unique data. Specific patient-food incompatibilities fall into many categories, and this Invention III, Capsule C provides for the small increment sampling, testing, patient-specific testing and system perturbation capability to evaluate and resolve such issues. Another area of importance is the impacts antibiotics and other ingested chemicals have within the gut environment at the point of application. The technology introduced by this Capsule C capability not only allows point, condition, and time specific delivery, but likewise, on the spot monitoring and partial analyses of results.

The stakes are high and the impacts of all these human health related issues reach all levels and aspects of our civilization. The second highest frequency of human diseases are associated with the gut, and over a period of time, the highest number of serious diseases are believed to originate in the gut directly, or indirectly as a result of conditions within the gut. This should place extremely high national and international priority upon developing the capability of efficient, cost-effective, and technically-effective gut sampling and diagnostic capabilities, and certainly with all aspects of patient considerations highly ranked in seeking solutions. This inventor actually suffers from some variation of gluten sensitivities, which actually led to this research and technology development project. There is also an even greater motivation. Undiagnosed gluten sensitivity conditions also caused misery for several years, and ultimately led to the cause of death of both of his parents. Therefore, the research leading up to this invention and its development is heavily engendered with passion and urgent concern for patients. However, as a career research engineer fortunately versed in several disciplines including biomechanics, this technology is also being developed with an unusual history of understanding, and an intrinsic level of experience with the processes and related issues, as well as, the types of new technologies needed. He has conducted extensive experiments with diet on his own body and documented the results, and formed many hypotheses pertaining to the fundamental causes of said illnesses and diseases. This invention is therefore, based upon addressing this national and world-wide need for improving human health in a realistic, meaningful, methodical, urgent, technology-based, and results-oriented manner.

The first invention by Shuck (U.S. patent Ser. No. 13/691,169) of which this is a continuation, was a serious accomplishment toward this overall objective, and the second invention entitled, “In Vivo Device for Researching GI Tract Processes, Microbes, and Variables Associated with Digestion, Illnesses and Diseases” and referenced as Invention II Capsule B, was a second step toward researching the phenomena to reach some level of understanding of the actual causes of the illnesses, and providing researchers of all disciplines with a tool and the missing technology that would give them the best opportunity to be successful in such efforts within their areas of specialization. Further background, methodologies, and implication details of this multi-stage technology development project are explained in the above referenced documents.

SUMMARY OF THE INVENTION

This device and method is step 3 of developing a system to revolutionize gut diagnosis and treatment technology, and in the process discover the causes of gut-based diseases and treat them. This capsule C invention is a tool specifically designed for physicians to use to treat patients, and also in the process, generate massive data profiles of patient illnesses and diseases with all of the patient-specific data history that can be helpful in advancing medical science and understanding of the gut system, and its important roles in other human organ diseases. This device and method also uses a belt-pocket system to deliver substances or objects to the gut in specially designed pockets of belts for use either as part of diagnostic or treatment processes, or functions to be performed as the Capsule passes through the gut, or to deliver medications in a safe and efficient manner to specific points, and based upon criteria as may be established to be sensed in vivo and interactively deployed, or as may be deployed by telemeter methods. This device known as Capsule C is a critical step in a continuing research project to develop a comprehensive gut health care system. Capsules A and B served more as impersonal basic science and research tools whereas, Capsule is a personalized focused diagnostic and treatment tool to be used by physicians in a clinical setting. In particular, this Capsule C can be allowed or commanded to, while in a particular region of the gut corresponding to specific anatomy or various criteria, release substances as prescribed by a physician of adequate quantity and protected from upper gut enzyme and acidic environments, thus of controlled composition and purity to be consumed, or interacted with microbes or other existing conditions within said region. Upon release, and simultaneously, or immediately after any prescribed time "$t_1$" following said medication or process delivery, begin to sample the associated microbes and chemical substances at prescribed time intervals $t_2$, $t_3$, etc. and preserve them for later in vitro analysis as feedback to physicians, to determine if the medications were successful as intended. In some cases, in vivo monitoring may provide proof of success of procedure, or indicate a needed iteration in procedure, of which in some cases, may be feasible. This capability requires a different apparatus with significantly different features, capabilities and methodologies from those of Capsules A and B, and different disciplinary medical educations by professionals utilizing the new patient examining and treatment tool. Special Capsule features include, for example, the delivery not only of medications, but new safe substances that may be effective in dissolving the viscoplastic encapsulating plaque like material that totally corrupts villi functions and leads to their disintegration, as evidenced in autopsied Celiac patients. Numerous special features in Capsule C enhance the success of application of this instrument to a wide range of gut conditions, and to achieve overall success of each of a multiplicity of purposes and candidate missions. Whereas Capsules A and B functions and applications were directed toward healthy and unhealthy individuals for largely research purposes, the functionality of Capsule C is focused entirely upon providing patient diagnosis, treatment, and results measurement, for ill or unhealthy individuals. Toward these design guidelines, it is human factor engineered exclusively for medical personnel use. Applications for Capsules A and B included largely exploring conditions in the gut in an "as is" and undisturbed condition, or creating a research-based modification or perturbation and measuring precisely the results, and involving multidisciplinary researchers in medical, biological and engineering sciences in order to plan the research experiments, acquire the desired research data, and analyze and interpret it. In contrast, Capsule C applications will normally include only practicing physicians and medical personnel who prescribe patient medications and protocols, for example, pre, during, and post diet control, or gut prep for purposes of medication administration and evaluating the effectiveness of the procedure, even as in an interactive mode. The belts and pockets in particular are designed from materials appropriate for specific medicinal substances, quantities, sequences, and monitoring means, and adapted conventional physician and pharmaceutical methodologies and protocols.

DETAILED DESCRIPTION OF INVENTION

Introduction

This Invention III was earlier referenced as Capsule AB, but for herein and future reference, is called Capsule C. The first two inventions, Capsules A and B were intended as exploratory research tools. This is the first attempt to provide practicing physicians with an efficient, safe, cost-effective in vivo tool to use for patient diagnostics and treatment. Whereas in Capsule B, significant research planning, spanning many disciplines of medicine and engineering, may be desirable for utilizing all of the capabilities provided, this Capsule C is intended and focused to serve both current off-the-shelf prescription medication applications, and quickly deliver new medications invented and developed as a result of the new technologies and methodologies being provided by Capsules A, B and C.

Applications for Capsules A and B included largely exploring conditions in the gut in an "as is" and undisturbed condition and especially in healthy individuals the Capsules just "went with the flow". In unhealthy individuals, as well as, prepped individuals as part of a protocol to administer some specific process or medication, some special additional features of a capsule are desirable, if not necessary. For example, typical gut problems involving gluten related sensitivities may involve severe constipation or diarrhea. Just "going with the flow" may be a problem for administration of treatments or Capsule applications. Both gut prep and capsule features are important in such cases of abnormal gut function. Many gut malfunctions involving such well known diseases as IBS, Crohn's, Celiac, gluten sensitivities, allergies, and a variety of provoked autoimmune response conditions, etc. result in gut wall and general environment conditions that must be thoroughly considered apriori to the design and application of a capsule device. Gut processes are truly dynamic and transient and of a longitudinal distribution function in nature, as pertains both to microbes, and the normal chyme or gut substances resulting from the bio-digestion process. However, gut contents rapidly move through the gut in some illness cases, rendering the gut digestion process truly a dynamic, transient one, as opposed to a quasi-static or relatively steady-state one in an engineering sense, in terms of substance passage rate through sections of the GI tract. Such cases as rapid bloating an hour or two after a meal may result in large quantities of microbe generated gas, and low viscosity liquids with potential for rapid motion. In some cases, substances may be needed in belt pockets to otherwise inertly stabilize and maintain the position of Capsule C during some prescribed time interval at some specific gut location during which time appropriate treatments can be administered and test results performed, since virtually all drug administrations are time dependent processes with known reasonable approximation timeframes for absorption and associated processes to occur. Features of Capsule C and its applications reflect these and many other considerations.

General Features of Capsule C—with Contrast to Capsules A and B

1. A housing assembled similarly to Capsules A and B, but with fewer and larger ports that are generally closed and sealed by a belt compressed against the inside wall, except when specific indexed belt pockets are positioned to align and center with specific ports, creating full access of the pocket contents to the gut.

2. Special rescue substances of significant quantity may be contained in one or more belt pockets as in Capsule B, but specifically tailored to the gut conditions, as assessed by physicians as either pre-existing, or a result of a prep procedure associated with, or resulting from applications of medications.

3. Fewer belt pockets (ranging from 1 to 10) and much larger size, and 3 belts with associated internal housing component layout are configured to accommodate transport and administration of medications in quantities required to address the subject abnormal gut conditions or illnesses.

4. One or more substances of quantity or other provisions may be contained in belt pockets to stabilize both the position of the capsule while procedures are executed, and to create a form of shield or other protected section and environment suitable for applying and sustaining medication in desired purity or concentration for a prescribed period of time and may include inflatable means.

5. Capsule C components can be fabricated from a range of substances suitable to accommodate special purpose requirements of a broad range of medical applications. For example, the belt and pockets can be fabricated from basic food products normally consumed by humans, or substances approved by the FDA for medical applications in 3-D printers, or substances and designs suitable for transport of animate or inanimate treatments or medications, or substances inert to specific medications. Likewise the materials are chosen to facilitate the variety of mechanical, electrical, physical, and other properties, such as viscosity, surface affinity, and means of administration.

Commentary Note on General Design Features:

During our lifetime we have witnessed technology revolution in which miniaturization of fabricated devices incorporating small working and mating parts relied upon, for example, the very talented Swiss watch makers and highly skilled technicians with specialty machine and casting shops. We have already progressed by many orders of magnitude in electrical and electronic components shrinking of size and data density, and along with many orders of magnitude increase in capabilities, this represents a swing far greater than $10^8$ order during the past half century. Now, with the advent of 3-D and 4-D printing, nano, and bionanotechnology, we are entering a new era of merging technologies wherein miniaturization by orders of magnitude of physical size of complex machines, including bio-based ones, can have extreme capabilities. This herein newly introduced technology is already utilizing these early threshold developments of said new era technologies of miniaturization of mechanical devices in several ways, including micro motor devices, and lab-on-a-chip based technologies, in vivo large data acquisition and storage, and interactive procedure capabilities. As a result of these three inventions Capsules A, B and C, huge data sets mined from the gut in vivo conditions, along with all of the research and patient generated data, new Big Data technologies for characterizing and analyzing complex system behavior and constructing comprehensive models of the human gut for diagnostic, treatment and general scientific purposes become realistically achievable. So, the future is very promising for near-future revolutionary impacts to human health of youth of today just based upon discovering and curing gut-based diseases alone, given proper attention and mindsets by multi-disciplinary R & D teams.

Diagnostic Features

Normally, diagnostic procedures in any discipline imply the direct measurement of magnitude, geometry, or other characterizing features. The normal temperature of a human body in quasi-steady state condition could be considered as being measured directly. However, certain autoimmune responses in humans are often measured indirectly, such as a function of temperature by thermometers, in which case a temperature increase may be considered as a reactive "perturbed" behavior measurement. In inanimate objects and non-reactive or passive processes, in general, measurements of matter order are direct. In reactive systems, including animate forms low in the phylogenetic tree to the cellular level, and maybe below, communications and other processes may be considered "reactive" and subject to responding when perturbed or provoked. This characteristic of biological systems gives extreme latitude for designing multidisciplinary reactionary response sensors and transducers indicative of a plethora of phenomena that may be considered as diagnostic for the presence or existence of some order/disorder or behavior of matter. It is with this broad interpretation and focus that guides this invention, and should guide technology development associated with all aspects of human body gut behavior as a means of specificity and extraneous variable elimination. Therefore, the direct measurement of gut matter order and behavior can be achieved from specifically designed, belt pockets containing conventional sensors and transducers, for direct measurement of, for example, such variables as temperature, pressures of a variety, surface tension, and other mechanical, physical, chemical, electrical, optical properties, with negligible Capsule C modifications.

Perhaps, the most important and greatest variety, for gut matter order and behavior assessment for diagnostic purposes, resides within the broad spectrum of possibilities involving reactive and perturbed response methodologies. This may be the most immediate and realistic approach to assessing gut phenomena associated with Celiac, gluten sensitivities, autoimmune responses, and the coupled and interdependent roles of microbes. In fact, separation of these phenomena and the huge multiplicity of variables in the in vivo environment, appears essential to determination of cause/effect relationships, and highly improbable by any conceivable extra-body in vitro means, especially such currently-used and technology-limited methodologies as statistical correlation of hundreds of symptom-based dependent variables. Thus, provisions and features of Capsule C are intended to accommodate the use of reactive, perturbation-response methodologies for varieties of macro, micro, and animate forms, and all feasible phylogenetic tree levels. Specific examples include presentation of organic or inorganic compounds, and animate or inanimate forms of matter, individually, in sequences or combinations, and measuring the responses. The use of lab-on-a-chip based technologies, especially cells-on-a-chip, wherein the cells may be those of the patient are extremely exciting opportunities. Versatility of the basic belt multiple-pocket system, in adapting to interactive patient care, especially the use of multiple belts allocated to specific functions, also gives great flexibility and facilitates this objective.

Treatment Features

As in diagnostic strategy, treatment strategies must likewise be broad-based in perspective. Capsule C and its versatile remotely articulated belt pocket designs are focused on providing options within all of the above diagnostic rationale, so that multi and interdisciplinary teams of practicing physicians can have the flexibility essential to administering any envisioned treatment of specific location, sequence, time interval, or other conceivable criteria. At least these are the guiding principles with which Capsule C is conceptually designed and to be fabricated into an implement.

One unique feature of Capsule C is small onboard chip-based circuits connected to belt and pocket articulation means, and other pockets in an adjacent sensor/detector/transducer belt, such that deployment of substances contained within specific indexed pockets in adjacent belt pockets can be initiated and deployed in an automatic mode, based upon the sensing/detection of signals emanating from specific sensor belt pockets. This feature is considered important in many applications, because extra-body human control may not be as responsive or effective for various reasons as in vivo control, especially in reactive perturbation systems. This in vivo detection and control methodology capability is also available to curtail other actions based upon such criteria as may indicate for example, sufficient treatment has been successful and should be terminated. A simple example is that when a specific value of pH is measured, some pocket substance is immediately released for whatever purpose. Another example could be when microbes of a specific species or their byproducts have triggered a sensor/detector for some prescribed variable value or phenomenon, such as cells-on-a-chip sensor/transducer exposed to toxins, some action is automatically initiated ASAP to detect onset of some process. An example may be an onset associated with the beginning stage of toxin creation, and then a pocket may be immediately closed and sealed at that instant in an interactive mode, thereby capturing the toxins and microbes, and as may be so designed, release an antibiotic at the exact point in the gut where the source of the problematic process exists as a treatment procedure.

Result Measurement Features

A practicing physician must be able to evaluate to the greatest extent possible the merits and success of any patient treatment. A belt with up to 10 large pockets is provided for sensors of suitable property measurement means that can be exposed upon command to monitor and to indicate when pre-established values of specific variables have been attained as may be specified by endocrinologists or other attending physicians.

An orally ingested capsule is designed to be user friendly specifically by medical personnel to quickly and efficiently diagnose patients with illnesses or diseases of the gut, wherein the capsule is comprised of actuator articulated belts and indexed pockets with onboard autonomous and telemeter controlled circuitry that can administer medication, and sample gut matter or measure gut system responses prior to, during, and after said medication or a system perturbation substance is delivered to the gut. Focus in this configuration is upon the gut contents matter and its consequential impact.

The capsule is comprised of multiple belts, each with a plurality of pockets of different design shapes and sizes to meet requirements and provide flexibility in obtaining samples of suitable quantity or other quality and preserved suitable for in vitro conventional laboratory analyses for both biochemical substances and microbial content, in order to provide quick, simple, and inexpensive diagnostic patient care. The sampling and medication operations are individually controlled by remote telemetry, and can be executed at any time "t" or any location "x" along the GI tract, and time intervals for performed operations are optional.

One configuration of belt-pocket systems includes three side-by-side belt-pocket systems, with the center belt-pockets containing medications or perturbation substances, and the two outside belt-pockets straddling the center one contain a variety of sensors to monitor gut fluid properties or body regional in vivo environment variables of interest as pertain to the specific medical procedure, including any variables as may be affected by said particular medication/substance delivery. The two monitoring belts with pocket sensors are positioned on each side (upstream and downstream) of medications/substance carrying belt and pocket system. One or more of these pockets may contain chip-based sensors/transducers, data reduction and logic circuits, nanobio sensors/transducers and cells-on-a-chip sensors/transducers. This configuration of this system is designed for particular medical logistical procedures, such as a body system perturbation to provoke body reaction responses, wherein "reactive" variables are measured, and all components are specifically sized and configured for these special purposes, and extra body functions and variables are also simultaneously measured for a wide variety of reasons. The capsule is designed to function independently of its orientation in the GI tract.

In another configuration two conventional belt-pocket matter sampling and preserving units straddle the medication/substance delivery belt-pocket system, one upstream and one downstream. This configuration is designed for particular medical logistical procedures, and optional autonomous or remote interactive substance delivery, largely involving microbial implication examinations, and all of the components are specifically sized and configured for these special purposes, and a variety of interchangeable cards are available for physician choices. One of the two belt-pocket systems straddling the center medication/substance delivery belt-pocket system, contains a belt-pocket matter sampling and preserving unit while the other straddling belt-pocket system positioned on the other side of center belt contains sensors. One or more of these pockets may contain chip-based sensors/transducers, data reduction and logic circuits, nanobio sensors/transducers and cells-on-a-chip sensors/transducers. This system is designed for particular medical logistical procedures, and optional autonomous or remote interactive substance delivery, largely involving microbial implication examinations, and all components are specifically sized and configured for these special purposes, and a variety of interchangeable cards are available for physician choices.

One or more components of ingested Capsules A, B, or C may be fabricated from normal food products, and/or FDA approved products for biomedical applications including for 3-D or 4-D printers. The instrumentation pockets may contain onboard chip-based data processing, reduction, and conversion, or logic circuits for expediting telemetry operations or onboard decision making.

A physician in the interest of quickly and inexpensively getting to a conclusion or decision point for an ill patient, can prescribe a specific belt/pocket configuration for deployment at a specific point x, perhaps including medication provisions, and collect samples or administer medication, or a perturbation, in order to form a basis of comparison to a particular healthy human gut profile or some distribution function of a plurality of variables, either as a diagnostic or a treatment procedure.

A prescribed configuration of Capsule components and contents is administered, in general and with protocols based upon a gut distribution function of a variety of variables, as may have been generated from some research data base, or the subject patient being treated.

A separate off-the-shelf belt and pocket system with various combinations of the capsule with actuator articulated belts and indexed pockets with onboard autonomous and telemeter controlled circuitry that can administer medication, and sample gut matter or measure gut system responses prior to, during, and after said medication or a system perturbation substance is delivered to the gut, with all of the features of this system having different focus and configured with different features to achieve specific "gut system perturbation responses" pertaining to specific GI tract anatomy. The strategy and methodology herein embodied is to test the patient for sensitivities, autoimmune, or other physical, chemical, biochemical, or other types of reactions by subjecting some chosen anatomical parts or regions of the gut to some specific perturbing or provoking substance or microbe, and measuring responses using onboard sensors. The focus of these configurations is the GI tract itself as opposed to the content matter. This in vivo procedure is somewhat analogous to simpler and older in vitro methods of using scratch or skin tests to determine food, or other substance allergies.

The substance delivery pockets may be larger in number and contain smaller quantities to test at low dosage levels, and a few pockets of larger size to contain larger quantities of same or different substances, and in some configurations, the belt passes over a guide idler roller bearing that pushes the belt against the selected and aligned housing port and in the process ruptures a very thin substance containing/confining film membrane covering said pockets, and thereby extrudes significant quantities of said substances into the precise desired section "x" of the gut, and the above provisions of either sampling or monitoring as apriori selected are implemented. The belts and pockets are co-designed by multi and interdisciplinary medical personnel and physicians ranging from neurologists, endocrinologists and allergists to microbiologists and may be so filled, situated, and indexed so that iterative or repetitive tests or treatments may be conducted using stepping or reversible micro-motors for either, repeatability-verification, required larger volumes, dosages, or concentrations of medications to achieve results, or other purposes as physicians may prescribe germane to their field of specialization.

At least one of a patient's prior determined distribution functions (DF) as measured by Capsules B or C, are stored on a chip, or lab-on-a-chip, and incorporated in logic circuits for triggering, subject to some parameter value within the specific DF being met to actuate some diagnostic or treatment procedure, thereby automating the process.

The capabilities and flexibilities introduced by these aforesaid belt and pocket systems are most effectively carried out within a framework of a rigid-body housing structure for precision and low-tolerance control purposes. However, some applications may require other versions of Capsule C in particular, for medication delivery, especially to smaller animals and younger humans. Other considerations are therefore given to capsule housing and internal structural components, such as, flexibility, collapsibility, inflatability, dilatability, dissolvability, digestibility, and what the achievable limits are. Today's peripheral technologies, have motor sizes of about 6 mm diameter but that may change. Constraints imposing such necessary considerations for more diverse applications of capsules include such things as convoluted folds and sharp bends of small and large intestines in smaller animals. Thus, other manifestations of said capsule designed features, although typically with less precision, include providing many other off-the-shelf versions of said capsules to be responsive to physician needs as part of a comprehensive gut in vivo healthcare delivery system.

Many of the structural components of Capsule C may be thin, inflated, flexible membranes and tubing with total capsule system integrated structural engineering designs, and of a diversity of dissolvable substances. Some members may be inflated and pressurized with liquids or gasses prior to ingestion, and some members or pockets may be in vivo inflatable for storage of, and using, sampled gut fluids, and the capabilities may be used as part of the sampling or delivery missions, or for safety and retrieval means. In addition, the designs and capabilities may be used for capsule stability during performance of prescribed functions.

Capsule C Features Summary

In summary, specificity of intricate design features is difficult because of contingencies based upon specific applications as may be envisioned, designed and developed for this Capsule C application by physicians or pharmaceutical companies. Thus, this invention, by virtue of its basic construction, possesses a unique quality of responsive off-the-shelf adaptability and versatility, with a diversity of belts, pockets and chip-based logic, sensors/transducers, control circuits, and data storage capability, as one of its valuable and useful features for meeting the technology needs for the broad-spectrum medical community. It is also intended to be of such basic design to quickly respond to evolutionary treatments resulting from this newly introduced technology. The technology enabling and catalyst roles of this diagnostic and treatment tool, is also especially noteworthy, as will be further discussed in Invention 4.

What is claimed is:

1. An interactive diagnostic and treatment device for at least one of perturbing, measuring and dispensing substances along an intestinal tract of a user, the device comprising:

a capsule configured to be swallowed and passed through the intestinal tract, the capsule including:

a housing defining an opening adapted to allow the substances to pass into and out of the housing, at least one sensor transducer, at least one belt disposed within the housing and defining a plurality of indentations, each of the indentations having a volume configured to perform at least one of collecting and dispensing the samples of matter, and at least one of a motor and an accuator disposed within the housing and an onboard autonomous and telemeter controlled circuitry.

2. The device of claim 1, wherein the belt allows mass delivery, collection, and measurement and analysis of substances.

3. The device of claim 1, further comprising multiple belts, with a plurality of pockets of different shapes and sizes to sample different amounts.

4. The device of claim 1, wherein the indentations contain a sealed environment capable of storing solids, liquids and gases and controlling the release of solids, liquids or gases.

5. The device of claim 1, further comprising a time release mechanism.

6. The device of claim 1, wherein there are at least three belt-pockets units, wherein two of the units contain sensors monitoring the external GI tract environment and one unit contains medications or perturbation substances.

7. The device of claim 6, wherein the units are positioned on each side for delivering medications or perturbations substances from one unit and configured to immediately measuring reactions.

8. The device of claim 7, configured to immediately deliver medications.

9. The device of claim 8, wherein the units are interchangeable cards.

10. The device of claim 1, further comprising at least one of onboard chip-based data processing, reduction and conversion.

11. The device of claim 1, wherein the device is configured to diagnose sensitivities, autoimmune or other in vivo reactions in the GI tract.

12. The device of claim 1 further comprising a guide idler roller to rupture a thin substance containing membrane and extrudes substances into precise areas of the GI tract.

13. The device of claim 1, wherein the pockets are filled, situated, and indexed so that iterative or repetitive tests or treatments may be conducted using at least one stepping or reversible micro-motors for at least one of repeatability-verification, larger volumes of medications.

14. The device of claim 1, further comprising a flexible membrane and tubing capable of being pressurized.

15. An interactive diagnostic and treatment method for perturbing, measuring, diagnosing and treating along an intestinal tract of a user, the method comprising:

providing a capsule configured to be swallowed and passed through the intestinal tract, the capsule including:

a housing defining an opening adapted to allow samples of matter to pass into and out of the housing, at least one sensor transducer, a belt disposed within the housing and defining a plurality of indentations, each of the indentations having a volume configured to collect or dispense the samples of matter, and a motor or actuator disposed within the housing, inserting the capsule into the intestinal tract, and continuously monitoring and reacting to the responses and an onboard autonomous and telemeter controlled circuitry.

16. A diagnostic and treatment system comprising a capsule configured to be swallowed and passed through the intestinal tract, the capsule including:

a housing defining an opening adapted to allow samples of matter to pass into and out of the housing, at least one sensor transducer, a belt disposed within the housing and defining a plurality of indentations, each of the indentations having a volume configured to collect or dispense the samples of matter, and an onboard autonomous and telemeter controlled circuitry for processing data and generating a 3-dimensional image using the data and delivering medications to identified areas.

* * * * *